US00PP36209P2

(12) United States Plant Patent
Bennett

(10) Patent No.: US PP36,209 P2
(45) Date of Patent: Oct. 22, 2024

(54) ***ROSA HYBRIDA* SHRUB PLANT NAMED 'AUSCP17117'**

(50) Latin Name: *Rosa hybrida*
Varietal Denomination: AUSCP17117

(71) Applicant: David Austin Roses Ltd., Wolverhampton (GB)

(72) Inventor: Carl Bennett, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 18/445,537

(22) Filed: Sep. 29, 2023

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
CPC ..... A01H 5/0222
See application file for complete search history.

(56) References Cited

PUBLICATIONS https://www.alexandrafarms.com/post/meet-hettie-a-vibrant-new-variety-from-david-austin-wedding-roses; Aug. 23, 2023; 1 page.*
https://theproducenews.com/floral/alexandra-farms-garden-roses-win-five-awards-safs-annual-outstanding-varieties-competition; Sep. 25, 2023; 1 page.*
https://www.floraldaily.com/article/9559096/alexandra-farms-garden-roses-win-five-awards-at-saf-s-varieties-competition/; Sep. 13, 2023; 2 pages.*
CPVO Application Consultation Version 4.17.23 Citation for 'AUSCP17117'; Apr. 18, 2024; 2 pages.*

* cited by examiner

*Primary Examiner* — Kent L Bell

(57) ABSTRACT

A variety of rose plant of the shrub class, named 'AUSCP17117'. The 'AUSCP17117' is a variety of a cut rose bearing large blooms with a deep pink color and a light fragrance with a long vase life.

1 Drawing Sheet

Classification: The present invention relates to a new *Rosa hybrida* shrub of the market class 'English Rose'.

Variety denomination: The new plant has the varietal denomination 'AUSCP17117'.

ORIGIN OF INVENTION

This invention relates to a new and distinct variety of shrub rose plant named 'AUSCP17117', which was originated from the cross-pollination of the two 'unnamed' and unpatented seedlings of *Rosa hybrida* in Albrighton, United Kingdom in 2018.

BACKGROUND OF THE INVENTION

The primary objective of this breeding was to produce a cut rose variety bearing large blooms with a deep pink color and a light fragrance with a long vase life.

SUMMARY OF THE INVENTION

Among the features which distinguish the new variety from others presently available and commercial rose cultivars known to the inventor is the following combination of characteristics: deep pink colored blooms that are many petalled with very large double blooms, strong stems, a light fragrance and growth habit suitable for cut rose production.

Asexual reproduction of the new variety by cutting taken from stems as performed in Albrighton, United Kingdom shows that the foregoing and other distinguishing characteristics come true to form and are established and transmitted through succeeding asexual propagations. 'AUSCP17117' may be asexually propagated by cuttings taken from stems.

COMPARISON WITH PARENTS

The maternal and paternal parents of 'AUSCP17117' are two unnamed seedlings. The new rose may be distinguished from its seed parent, by the following combination of characteristics: the seed parent has a flower which is mid-pink in color, with fewer petals, whereas 'AUSCP17117' is a deep pink color and has a much longer vase life when cut from the plant. The new rose may be distinguished from its pollen parent, by the following combination of characteristics: the pollen parent is yellow in color with a hybrid tea bloom form, whereas 'AUSCP17117' is a deep pink color with a more rounded old rose style bloom.

COMPARISON WITH THE CLOSEST COMMERCIALLY AVAILABLE CULTIVAR

The most similar rose variety is 'AUSapply' (U.S. Plant Pat. No. 29,958). 'AUSapply' typically has an irregularly rounded bloom form, as opposed to the more rounded form of 'AUSCP17117'. 'AUSapply' also exhibits a stronger fragrance as compared to the very weak fragrance of 'AUSCP17117'. The petal count between the two roses is also different, with 'AUSapply' having approximately 100 petals per bloom, and 'AUSCP17117' has approximately 120 petals per bloom. Finally, 'AUSapply' has a predominant stamen color that is white, whereas 'AUSCP17117' has a predominant stamen color that is yellow.

BRIEF DESCRIPTION OF ILLUSTRATION

The accompanying photograph illustrates the new variety and shows the flowering thereof from bud to full bloom for a 5-year-old rose plant of the new variety. The photograph is depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of cut 'AUSCP17117' specimens were made in a greenhouse in Albrighton, Wolverhampton, United Kingdom. The following description is of 5-year-old rose plants of the new variety grown in a greenhouse environment in Albrighton, United Kingdom in the month of May. Phenotypic expression may vary with environmental, cultural and climatic conditions, as well as differences in conditions of light and soil.

FLOWER CHARACTERISTICS

Blooming habit: Continuous. The number of blooms per plant during the growing season is profuse, but there are too many to count.

Bud:

*Size*.—About 2.7 cm long and 2.1 cm in diameter when the petals start to unfurl.

*Form*.—The bud form is short pointed ovoid.

*Color*.—When sepals first divide, the bud color is RHS 59B (red-purple group). When half blown, the upper sides of the petals are RHS N66A (red-purple group), and the lower sides of the petals are RHS 61B (red-purple group).

*Calyx*.—Shape: opens as a star shape and folds back against the stem. Length: 7.1 cm. Diameter: 7.1 cm.

*Sepals*.—Arrangement: Regular. Color: Upper Surface: RHS 144B (yellow-green group). Lower Surface: RHS 144B (yellow-green group). Length: 2.8 cm. Width: 1 cm. Shape: Acuminate. Apex: Lanceolate. Margin: predominantly hairy. Surface texture: Upper Surface: smooth, slightly hairy. Lower Surface: smooth. Number: There are 2 lightly appendaged sepals, and 3 unappendaged sepals with hairy edges.

*Receptacles*.—Color: RHS 143A (green group). Shape: Apple. Size: Large, about 1.7 cm long×1.6 cm wide. Surface: Smooth.

*Peduncle*.—Length: Long, averaging about 9 cm. Diameter: 0.4 cm. Surface: Smooth. Color: RHS 144A (green-yellow group) with coloration of RHS 184A (greyed-purple group) towards the bottom of the peduncle. Strength: Normal.

Blooms:

*Size*.—Large, average open diameter is about 11.5 cm and average depth is about 3.2 cm.

*Borne*.—Singly with the other blooms being nipped out for single bloom cut rose production.

*Form*.—When first open, bloom is cupped. Permanence of bloom flattens: outer petals curl slightly.

Petalage: Number of petals under normal conditions: approx. 120.

*Color*.—The upper sides of the petals are RHS N66B (red-purple group). The reverse sides of the petals are RHS 64C (purple group). The base of the petals has a very small basal spot that is RHS 2C (yellow group) in color.

*Variegations*.—None.

*Discoloration*.—The general tonality at the end of the first day is RHS N66A (red-purple group), and at the end of the third day is RHS N66B (red-purple group).

*Fragrance*.—Slight. Character of fragrance: Not sufficient to characterize.

Petals:

*Texture*.—Smooth inner side and rough outer side.

*Size*.—Width: 4.1 cm. Length: 3.7 cm.

*Surface*.—Smooth/Rough as described above.

*Shape*.—Round (outer petals); Obcordate (middle petals).

*Margin*.—Entire.

*Apex shape*.—Cuspidate.

*Base shape*.—Rounded.

*Form*.—Tips slightly recurved.

*Arrangement*.—Informal.

*Petaloids*.—Number: approx. 15-20. Color: RHS N66B (red-purple group). Length: 1.5 cm. Width: 0.5 cm. Shape: Obovate. Margin: Irregular.

*Persistence*.—Petals drop off cleanly before drying.

*Lastingness*.—On the plant: not tested. As a cut flower: very long about 10-12 days.

Reproductive parts:

*Stamens*.—Number: approximately 90. Length: approximately 0.8 cm.

*Anthers*.—Length: approximately 0.6 cm. Color: RHS 13A (yellow group). Arrangement: mixed with petaloids.

*Filaments*.—Color: RHS 13A (yellow group). Length: 0.1-0.2 cm.

*Pollen*.—Color: RHS 9C (yellow group). Amount: scarce.

*Pistils*.—Number: approximately 120. Length: approximately 0.9 cm.

*Styles*.—Color: RHS N155A (white group) with apex of RHS 62B (red-purple group). Length: 0.8 cm.

*Stigmas*.—Color: RHS 13C (yellow group). Length: approximately 0.1 cm.

*Hips*.—NONE observed.

PLANT CHARACTERISTICS

Plant form: Shrub.

Plant growth: Vigorous and upright.

Age to maturity: 2 years.

Mature plant: Height: 130 cm. Width: 70 cm.

Rootstock: Own root (production from cuttings) for the roses observed in the United Kingdom.

Foliage:

*Number*.—Leaflets on normal mid-stem leaves is: even split of 5 and 7 (including terminal leaflet).

*Size*.—Large, about 20.5 cm long×14.25 cm wide.

*Quantity*.—Normal. Number of leaves per flowering stem is: approximately 7-8.

*Color*.—New foliage: Upper side: RHS 146A (yellow-green group) with a perimeter of RHS 60A (red-purple group). Lower side: RHS 146D (yellow group) with a perimeter of RHS 60A (red-purple group). Old foliage: Upper side: RHS 147A (yellow-green group). Lower side: RHS 147B (yellow-green group).

Leaflets:

*Size*.—About 7.5 cm long×5.5 cm wide.

*Shape*.—Pointed oval.

*Base shape*.—Rounded.

*Apex shape*.—Acuminate.

*Texture*.—Upper side: Leathery. Lower: Leathery.

*Edge*.—Serrated.

*Serrations*.—Single/Large.

*Petiole*.—Color: Perimeter is RHS 143B (green group) reverse and outer, and central vein is RHS 153D (yellow-green group). Length: 5.1 cm. Width: 0.2 cm. Upper Surface Texture: Smooth, slightly glandular. Lower Surface Texture: Smooth.

*Petiole rachis*.—Color: RHS 143A (green group) outer and reverse, and center is RHS 153D (yellow-green group). Length: 4 cm Diameter: 0.2 cm Underside: smooth with prickles. Lower surface texture: smooth.

*Stipules*.—Length: 1.5 cm. Type: Lateral. Apex: Acute. Color: RHS 143B (green group).

*Auricle*.—Shape: Lanceolate. Length: 0.5 cm Width: 0.1 cm. Color: RHS 143B (green group).

*Vein color*.—Central vein RHS 151A (yellow-green group), rest of venation RHS 147A (yellow-green group).

*Venation pattern*.—Reticulate.

Wood:

*New wood*.—Color: RHS 183D (greyed-purple group) with flashes of RHS 146C (yellow-green group). Bark: Smooth.

*Old wood*.—Color: Bottom ⅓ is RHS 146A (yellow-green group) and Upper ⅔ is RHS 200C (brown group). Bark: Smooth.

Branching habit:

*Number*.—Not applicable.

*Dimensions*.—Not applicable.

Stems:

*Mature stem*.—Length: 120 cm. Diameter: 0.9 cm.

*Internode distance*.—5.3 cm. The above measurements are all variable, depending on growing conditions in a season.

*Stem pubescence present*.—No.

Prickles:

*Quantity*.—On main canes from base: ordinary/few. Number per stem length: 10-12 per 20 cm.

*Form*.—Deep concave.

*Length*.—0.9 cm.

*Width*.—0.8 cm.

*Color when young*.—RHS 60A (red-purple group).

*Color when mature*.—RHS 60A (red-purple group) with RHS N144B (green-yellow group) at apex.

Small prickles:

*Quantity*.—Main stalk: None. Laterals: not applicable.

Disease resistance:

*Powdery mildew* (*podosphaera pannosa*).—Resistant.

*Downey mildew* (*peronospora species*).—Resistant.

*Blackspot* (*diplocarpon rosae*).—Resistant.

*Rust* (*phragmidium tuberculatum*).—Resistant.

Pest resistance: Not tested.

Winter hardiness: Not tested.

Growing conditions: Normal greenhouse conditions for cut rose production.

What is claimed is:

1. A new and distinct variety of rose plant of the *Rosa hybrida* shrub plant named 'AUSCP17117', substantially as herein shown and described.

* * * * *

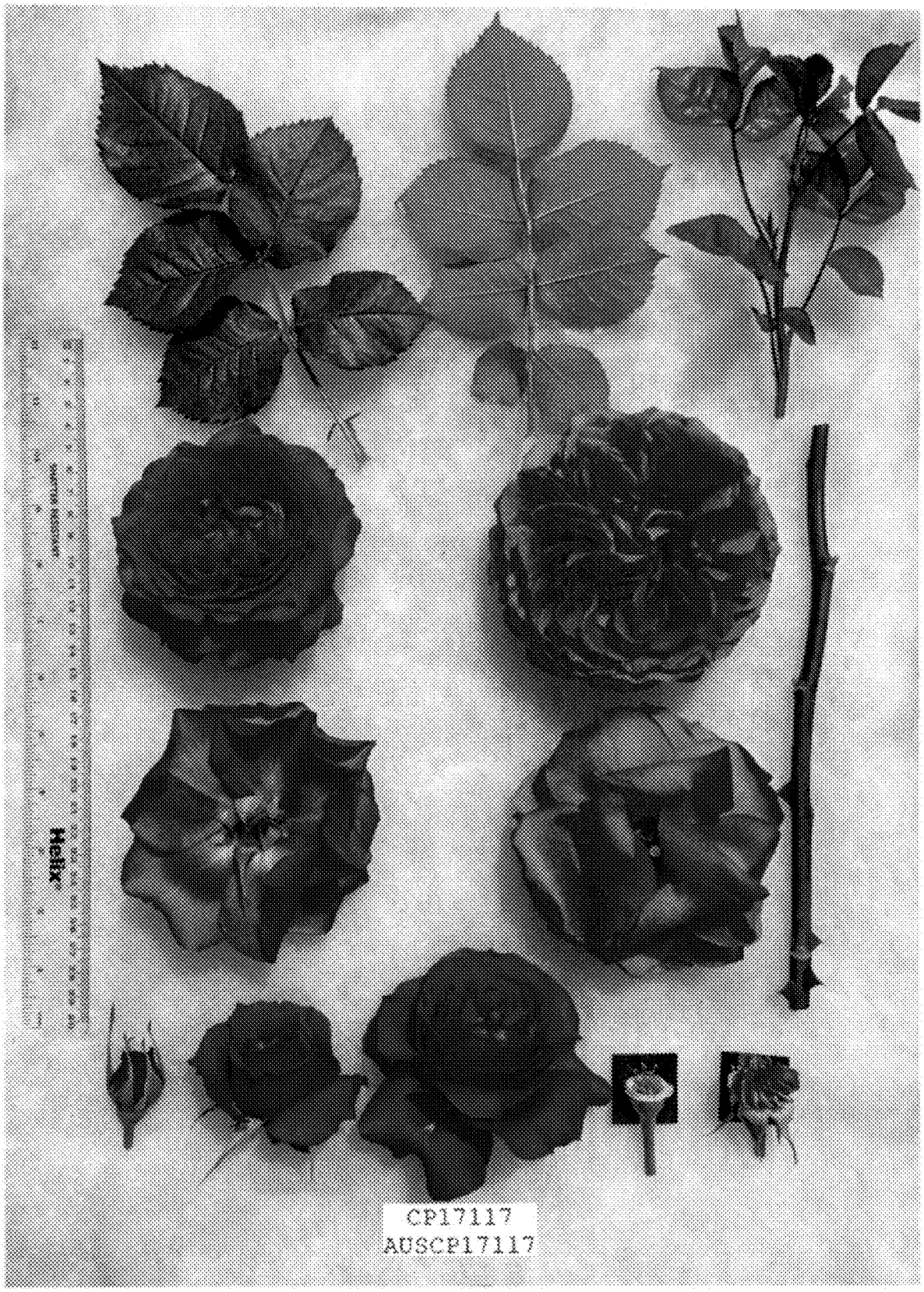
Helix
CP17117
AUSCP17117